United States Patent
Yu

(10) Patent No.: US 9,523,649 B2
(45) Date of Patent: Dec. 20, 2016

(54) DEVICE FOR AUTOMATICALLY INSPECTING LENS ELEMENTS OF OPTICAL CONNECTORS

(71) Applicant: HON HAI PRECISION INDUSTRY CO., LTD., New Taipei (TW)

(72) Inventor: Chen-Yu Yu, New Taipei (TW)

(73) Assignee: HON HAI PRECISION INDUSTRY CO., LTD., New Taipei (TW)

( * ) Notice: Subject to any disclaimer, the term of this patent is extended or adjusted under 35 U.S.C. 154(b) by 361 days.

(21) Appl. No.: 14/228,261

(22) Filed: Mar. 28, 2014

(65) Prior Publication Data

US 2014/0307942 A1    Oct. 16, 2014

(30) Foreign Application Priority Data

Apr. 10, 2013    (TW) .............. 102112603 A

(51) Int. Cl.
*G01B 9/00*    (2006.01)
*G01N 21/958*    (2006.01)
*G01M 11/02*    (2006.01)

(52) U.S. Cl.
CPC ........ *G01N 21/958* (2013.01); *G01M 11/0214* (2013.01); *G01N 2021/9583* (2013.01)

(58) Field of Classification Search
USPC .................................. 356/124–127
See application file for complete search history.

(56) References Cited

U.S. PATENT DOCUMENTS

2006/0238903 A1* 10/2006 Sato ................ G02B 7/023
359/824

* cited by examiner

*Primary Examiner* — Tri T Ton
(74) *Attorney, Agent, or Firm* — Zhigang Ma

(57) ABSTRACT

A device includes a holding device, a first camera module, a second camera module, a driving device, and an image processor. The holding device is configured for holding a plurality of lens elements, each of which includes lenses. The driving device is connected to the first camera module and the second camera module and configured for driving the first camera module and the second camera module to move such that the first camera module and the second camera module aim at and capture an image of each lens. The image processor is in communication with the first camera module and the second camera module and configured for processing the images to detect defects of the lenses, if any.

6 Claims, 3 Drawing Sheets

DEVICE FOR AUTOMATICALLY INSPECTING LENS ELEMENTS OF OPTICAL CONNECTORS

BACKGROUND

1. Technical Field

The present disclosure relates to optical connectors and, particularly, to a device for automatically inspecting lens elements of optical connectors.

2. Description of Related Art

Optical connectors include a number of photoelectric elements, a number of optical fibers, and a lens element. The lens element is positioned between the photoelectric elements and the optical fibers. The lens element includes a number of first lenses on a surface facing the photoelectric elements and a number of second lenses on a surface facing the optical fibers. Each first lens is optically coupled with one of the second lenses. Each photoelectric element is aligned with one of the first lenses and each optical fiber is aligned with one of the second lenses. As such, each photoelectric element can emit light to or receive light from the corresponding optical fiber via the corresponding first lens and the corresponding second lens to increase light usage efficiency. To ensure high quality, the lens element needs to pass an optical inspection to detect defects of the first lenses and the second lenses, if any. At present, the optical inspection is manually carried out, which is inefficient.

Therefore, it is desirable to provide a device for inspecting lens elements of optical connectors that can overcome the above-mentioned problems.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean "at least one." The references "a plurality of" and "a number of" mean "at least two."

Embodiments of the present disclosure will be described with reference to the drawings.

Figure 1:
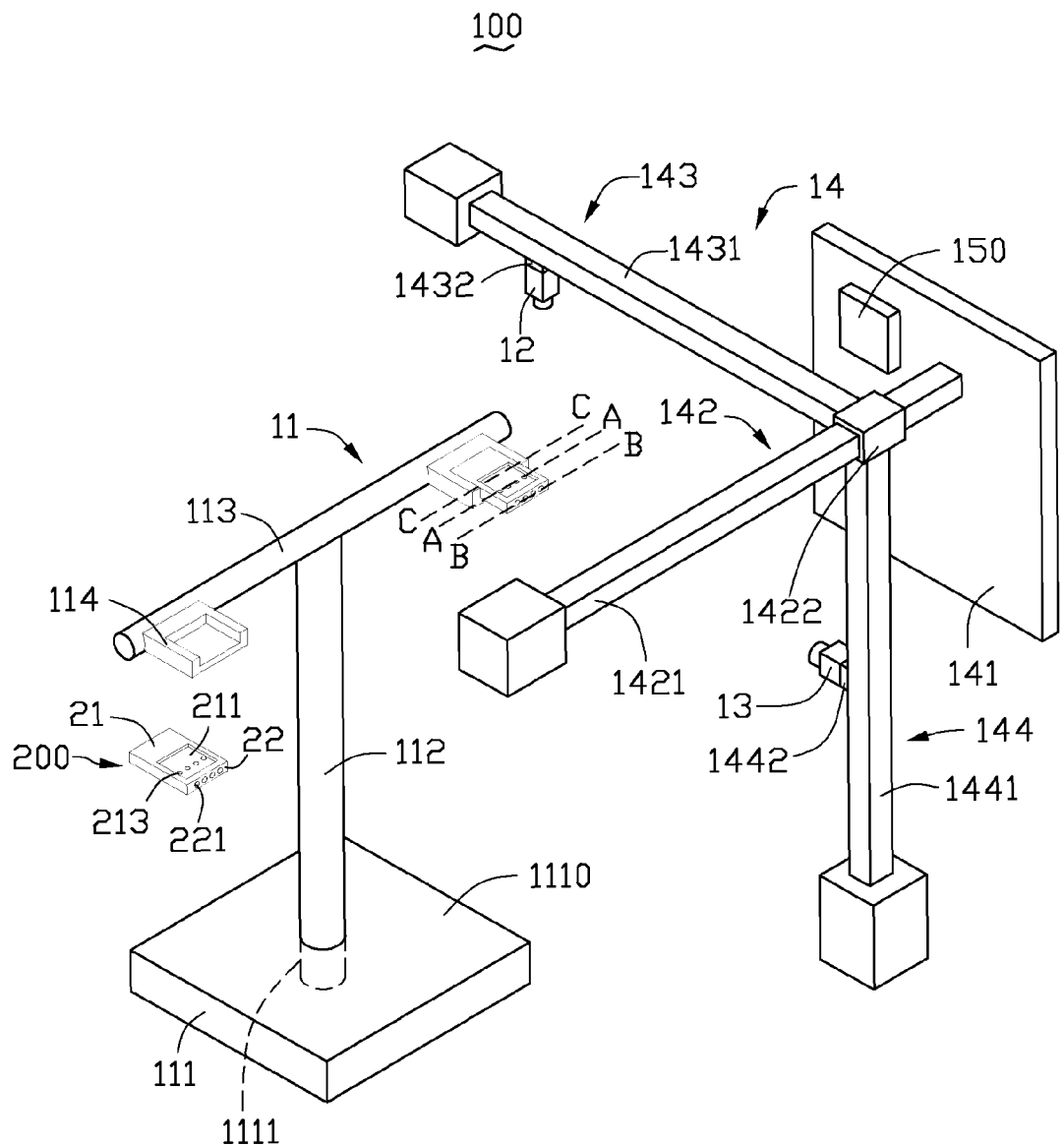
FIG. 1 is an isometric schematic view of a device for automatically inspecting lens elements of optical connectors, according to an embodiment.
Figure 2:
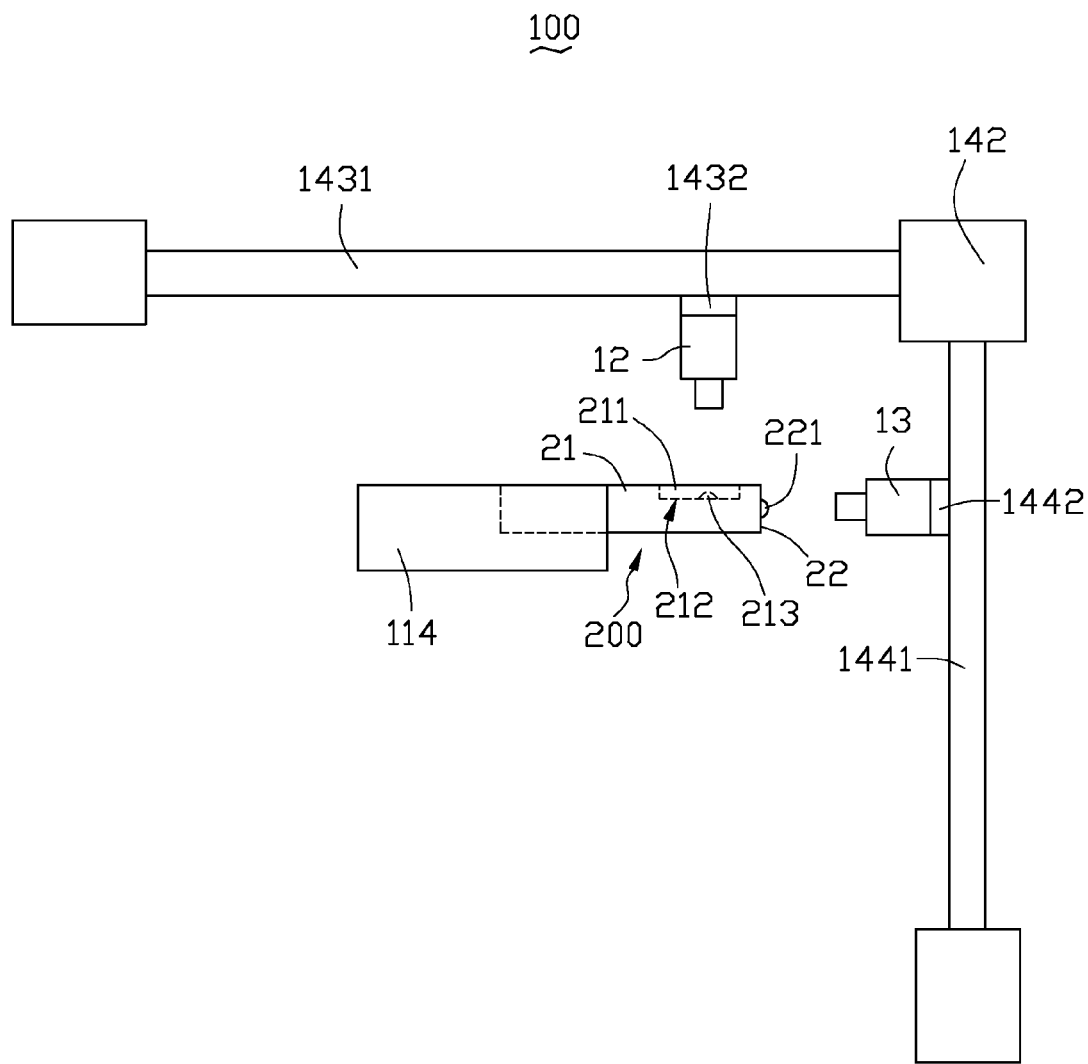
FIG. 2 is a planar view of the device and the lens elements of FIG. 1.

FIGS. 1-2 show a device 100 for automatically detecting defects of more than one lens element 200 at one time, according to an embodiment. In this embodiment, the number of the lens elements 200 is two.

The lens element 200 is made of transparent plastic by an injection molding technology.

In this embodiment, the lens element 200 is substantially rectangular and includes a first surface 21, and a second surface 22 perpendicularly connecting the first surface 21. The lens element 200 defines a substantially rectangular recess 211 in the first surface 21. The lens element 200 includes a number of first lenses 213 formed on a bottom surface 212 of the recess 211 and arranged along a first line AA, which is substantially parallel with the second surface 22. The lens element 200 also includes a number of second lenses 221 formed on the second surface 22 and arranged along a second line BB, which is substantially parallel with the first surface 21. In this embodiment, the number of the first lenses 213 is four but can be changed in other embodiments depending on need.

The device 100 includes a holding device 11, a first camera module 12, a second camera module 13, a driving device 14, and an image processor 15.

The holding device 11 is configured for holding the lens elements 200 along a third line CC that is substantially parallel with the first lines AA and the second lines BB. In this embodiment, the holding device 11 includes a base 111, a holding rod 112, a first cantilever 113, and two seats 114.

The base 111 is substantially rectangular and includes a top surface 1110. The base 111 defines a fixing hole 1111 in the top surface 1110.

The holding rod 112 is configured to fit into the fixing hole 1111, thus standing on the base 111.

A central part of the first cantilever 113 is fixed to an end of the holding rod 112 that is distant from the base 111.

The seats 114 are positioned at two distal ends of the first cantilever 113. Each lens element 200 can be seated in one of the seats 114.

As such, the lens elements 200 are held by the holding device 11 in the third line CC.

The driving device 14 is connected to the first camera module 12 and the second camera module 13 and is configured for driving the first camera module 12 and the second camera module 13 to move along the third line CC such that the first camera module 12 aims at and captures an image of each first lens 213 and the second camera module 13 aims at and captures an image of each second lens 221. In this embodiment, the driving device 14 includes a fixing board 141, a first linear driver 142, a first holder 143, and a second holder 144.

The fixing board 141 is substantially rectangular and fixed in place relative to the base 111 and substantially perpendicular to the third line CC.

The first linear driver 142 can be a linear motor and includes a first linear stator 1421 and a first slider 1422. An end of the first linear stator 1421 is fixed to the fixing board 141 and arranged along a direction that is substantially parallel with the third line CC. The first slider 1422 is slidably positioned on the first linear stator 1421. The first linear driver 142 is configured for driving the first slider 1422 to slide on the first linear stator 1421.

The first holder 143 is fixed to the first slider 1422 and arranged perpendicular to the third line CC and the holding rod 112. The first camera module 12 is held by the first holder 143 and aims at the first lenses 213.

The second holder 144 is fixed to the first slider 1422 and arranged perpendicular to the third line CC and parallel with the holding rod 112. The second camera module 13 is held by the second holder 144 and aims at the second lenses 221.

The image processor 15 is in communication with the first camera module 12 and the second camera module 13 and is configured for processing the image to detect defects of the first lenses 213 and the second lenses 221.

In operation, the driving device 14 can automatically drive the first camera module 12 and the second camera module 13 to move and capture the images of the first lenses 213 and the second lenses 221 for defect detection. As such, an efficiently of the defect detection is increased.

In this embodiment, the first holder 143 can also be a linear motor and includes a second linear stator 1431 and a second slider 1432. An end of the second linear stator 1431 is fixed to the first slider 1422. The second slider 1432 is slidably positioned on the second linear stator 1431. The first holder 143 is configured for driving the second slider 1432 to slide on the second linear stator 1431. The first camera module 12 is fixed to the second slider 1432.

The second holder 144 can also be a linear motor and includes a third linear stator 1441 and a third slider 1442. An end of the third linear stator 1441 is fixed to the first slider 1422. The third slider 1442 is slidably positioned on the third linear stator 1441. The second holder 144 is configured for driving the third slider 1442 to slide on the third linear stator 1441. The second camera module 13 is fixed to the third slider 1442.

As such, alignments between the first camera module 12 and the first lenses 213 and between the second camera module 13 and the second lenses 221 can be adjusted by the first holder 143 and the second holder 144.

Figure 3:
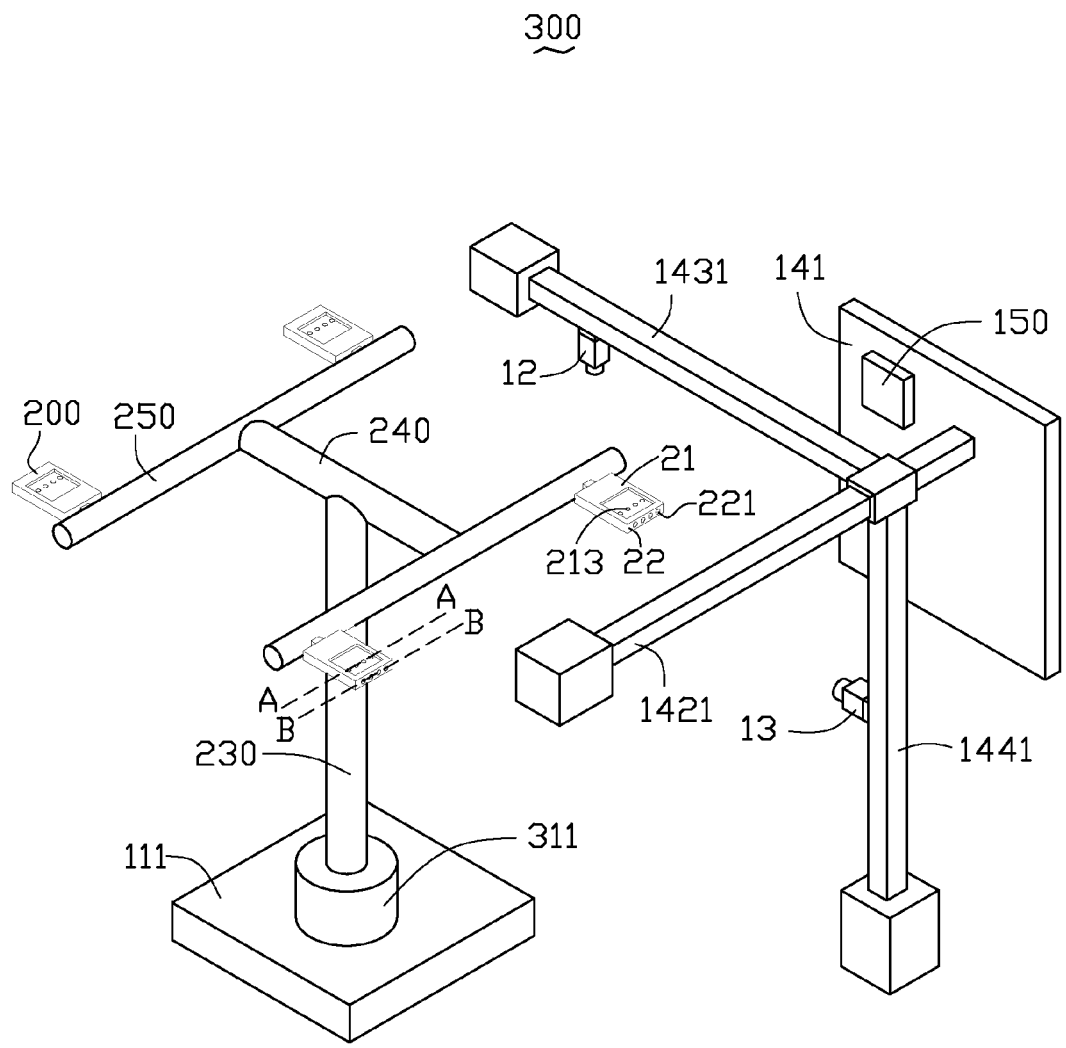
FIG. 3 is an isometric schematic view of a device for automatically inspecting lens elements of optical connectors, according to another embodiment.

FIG. 3 shows a device 300 for automatically detecting defects of the lens elements 200, according to another embodiment. In this embodiment, the number of the lens elements 200 is four. The lens elements 200 are connected by a runner system including a sprue rod 230, a main runner rod 240, and two branch runner rods 250. A central part of the main runner rod 240 is fixed to an end of the sprue rod 230. Central parts of the branch runner rods 250 are connected to two distal ends of the main runner rod 240. The lens elements 200 are fixed to distal ends of the branch runner rods 250. As such, the lens elements 200 are arranged into two third lines CC that are substantially parallel with the first line AA and the second line BB.

The device 300 is essentially similar to the device 100 except that the device 300 includes a holding device 31 which includes the base 111 and a rotating driver 311. The rotating driver 311 is positioned on the base 111 and an end of the sprue rod 230 that is distant from the main runner rod 240 is fixed to the rotating driver 311 such that main runner rod 240 is substantially parallel with the second slider 1432. The rotating driver 311 is configured for driving the sprue rod 230 to rotate.

The first holder 143 can drive the first camera module 12 to move to aim at the first lenses 213 in the different third lines CC. The rotating driver 311 can rotate the sprue rod 230 such that the second lenses 221 in different third lines CC face the second camera module 13. The second holder 144 can adjust the second camera module 13 to aim at the facing second lenses 221. As such, all of the first lenses 213 and the second lenses 221 of the lens elements 200 can be detected.

It will be understood that the above particular embodiments are shown and described by way of illustration only. The principles and the features of the present disclosure may be employed in various and numerous embodiments thereof without departing from the scope of the disclosure. The above-described embodiments illustrate the possible scope of the disclosure but do not restrict the scope of the disclosure.

What is claimed is:

1. A device comprising:
    a holding device configured for holding a plurality of lens elements, each lens element comprising a first surface, a second surface, a plurality of first lenses, and a plurality of second lenses, the first lenses arranged along a first line on the first surface, the second lenses arranged along a second line on the second surface that is perpendicularly connecting the first surface, the lens elements being arranged along at least one third line which is substantially parallel with the first lines and the second lines;
    a first camera module;
    a second camera module;
    a driving device connected to the first camera module and the second camera module and configured for driving the first camera module and the second camera module to move along each third line such that the first camera module aims at and captures an image of each first lens and the second camera module aims at and captures an image of each second lens; and
    an image processor in communication with the first camera module and the second camera module and configured for processing the images to detect defects of the first lenses and the second lenses, if any.

2. The device of claim 1, wherein the holding device comprises:
    a base defining a fixing hole;
    a holding rod fixed in the fixing hole;
    a first cantilever with a central part fixed to an end of the holding rod opposite to the base; and
    two seats positioned at two distal ends of the first cantilever, each lens element seating in one of the seats.

3. The device of claim 2, wherein the number of the lens elements is two and the driving device comprises:
    a fixing board fixed in place in relative to the base;
    a first linear driver comprising a first linear stator and a first slider, one end of the first linear stator being fixed to the fixing board, the first linear stator being substantially parallel with the at least one third line, the first slider being slidably positioned on the first linear stator, the first linear driver being configured for driving the first slider to slide on the first linear stator;
    a first holder fixed to the first slider and holding the first camera module such that the first camera module aims at the first lenses; and
    a second holder fixed to the first slider and holding the second camera module such that the second camera module aims at the second lenses.

4. The device of claim 3, wherein the first holder is a linear motor and comprises a second linear stator and a second slider, the second linear stator is fixed to the first slider, the second slider is slidably positioned on the second stator, the first holder is configured for driving the second slider to slide on the second stator, and the first camera module is fixed to the second slider.

5. The device of claim 4, wherein the second holder is a linear motor and comprises a third linear stator and a third slider, the third linear stator is fixed to the first slider, the third slider is slidably positioned on the third linear stator, the first holder is configured for driving the second slider to slide on the second linear stator, and the first camera module is fixed to the second slider.

6. The device of claim 1, wherein the number of the lens elements is four, the lens elements are connected by a runner system comprising a sprue rod, a main runner rod, and two branch runner rods, a central part of the main runner rod is fixed to an end of the sprue rod, central parts of the branch runner rods are connected to two distal ends of the main runner rod, the lens elements are fixed to distal ends of the branch runner rods, the holding element comprises a base and a rotating driver positioned on the base, an end of the sprue rod that is distant from the main runner rod is coupled to the rotating driver, the rotating driver is configured for driving the sprue rod to rotate.

* * * * *